United States Patent
Appling et al.

(10) Patent No.: US 11,821,820 B2
(45) Date of Patent: Nov. 21, 2023

(54) SPECIMEN COLLECTOR INCLUDING MULTIPLE SPECIMEN WELLS

(71) Applicant: EnTellect Medical Holdings, Louisville, KY (US)

(72) Inventors: Anthony Appling, Crestwood, KY (US); Ben Morris, Jeffersonville, IN (US); Gerald Dryden, Louisville, KY (US)

(73) Assignee: ENTELLECT MEDICAL HOLDINGS, Louisville, KY (US)

( * ) Notice: Subject to any disclaimer, the term of this patent is extended or adjusted under 35 U.S.C. 154(b) by 791 days.

(21) Appl. No.: 16/936,018

(22) Filed: Jul. 22, 2020

(65) Prior Publication Data

US 2022/0026315 A1 Jan. 27, 2022

(51) Int. Cl.
| | | |
|---|---|---|
| G01N 1/14 | (2006.01) | |
| A61B 10/02 | (2006.01) | |
| B01L 3/00 | (2006.01) | |
| G01N 1/10 | (2006.01) | |

(52) U.S. Cl.
CPC ............... *G01N 1/14* (2013.01); *A61B 10/02* (2013.01); *B01L 3/502* (2013.01); *A61B 2010/0225* (2013.01); *B01L 2300/0848* (2013.01); *G01N 2001/1031* (2013.01)

(58) Field of Classification Search
CPC .. G01N 1/14; G01N 2001/1031; A61B 10/02; A61B 2010/0225; B01L 3/502; B01L 2300/0848
See application file for complete search history.

(56) References Cited

U.S. PATENT DOCUMENTS

| | | | |
|---|---|---|---|
| 5,363,860 A | 11/1994 | Nakao et al. | |
| 8,088,079 B2 | 1/2012 | Kaye et al. | |
| 9,671,318 B1 | 6/2017 | Bedoe et al. | |
| 2008/0319341 A1* | 12/2008 | Taylor | A61B 10/0275 600/567 |
| 2009/0227893 A1* | 9/2009 | Coonahan | A61B 10/0283 600/566 |
| 2020/0188921 A1* | 6/2020 | Goodman | A61B 10/0045 |

\* cited by examiner

*Primary Examiner* — Eric F Winakur
*Assistant Examiner* — Jonathan Drew Moroneso
(74) *Attorney, Agent, or Firm* — Dickinson Wright PLLC

(57) ABSTRACT

A specimen collector for gathering tissue specimens includes a housing extending along a first axis between a first opening and a second opening to define a hollow interior. An inlet port and an outlet port are located axially between the first and second openings. A specimen tray defines a first specimen well and a second specimen well and is slideably disposed within the housing and axially slideable between a first position to dispose the first specimen well in fluid communication with the inlet and outlet ports and a second position to dispose the second specimen well in fluid communication with the inlet and outlet ports. The specimen tray comprises a pair of tray components each defining a respective one of the first and second wells and jointly slideable. The pair of tray components are separable from one another and each individually removable from the housing.

19 Claims, 7 Drawing Sheets

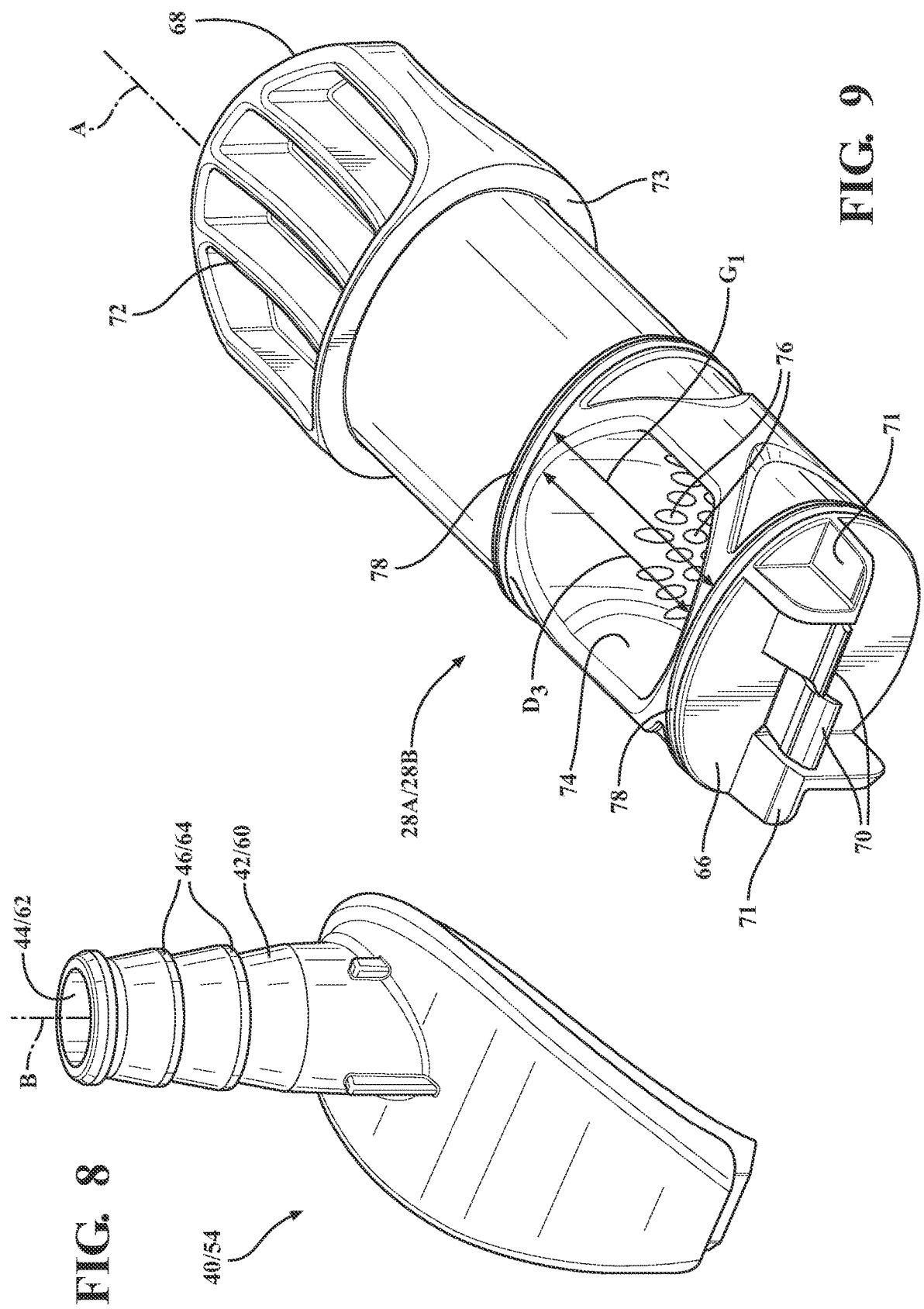

SPECIMEN COLLECTOR INCLUDING MULTIPLE SPECIMEN WELLS

BACKGROUND OF THE INVENTION

1. Field of the Invention

The subject invention relates to a specimen collector for use in medical procedures. More particularly, the subject invention relates to a specimen collector that includes multiple specimen wells for alternating the collection of tissue specimens during a medical procedure.

2. Related Art

Specimen collectors are used in medical operations, such as endoscopic polypectomies, where vacuum is utilized to gather tissue specimens from patients. U.S. Pat. No. 9,671,318 discloses an example of a specimen collector, which includes a housing that defines a hollow interior and extends along an axis between a first opening and a second opening. The housing further defines an inlet port and an outlet port, each fluidly communicating with the hollow interior and located axially between the first and second openings. The inlet port is connectable to a medical instrument for collecting tissue specimens from the patient, and the outlet port is connectable to a suction source for establishing a suction effect at the medical instrument. A one-piece specimen tray is slideable within the housing and includes a first specimen well and a second specimen well, each for gathering tissue specimens collected by the medical instrument. The specimen tray is moveable between a first position in which the first specimen well is in fluid communication with the inlet and outlet ports, and a second position in which the second specimen well is in fluid communication with the inlet and outlet ports.

However, an issue with such specimen collectors is that the specimen tray cannot be removed during the medical procedure, namely because a vacuum within the housing is lost upon the removal of the specimen tray. As such, the prior art devices require the medical procedure to be paused in order to remove and clean the specimen collectors, and then restarted, thus leading to a lengthy collection process when the gathering of multiple tissue specimens is required. Removal of the prior art specimen tray can also cause tissue specimens to be inadvertently delivered to the suction source in the event that the suction source isn't turned off prior to removal of the specimen tray. As such, there remains a need for improvements to such specimen collectors.

SUMMARY OF THE INVENTION

A specimen collector for gathering tissue specimens during a medical procedure includes a housing extending along a first axis between a first opening and a second opening to define a hollow interior. The housing includes an inlet port and an outlet port each fluidly communicating with the hollow interior and located axially between the first and second openings. A specimen tray defines a first specimen well and a second specimen well and is slideably disposed within the housing and axially slideable between a first position to dispose the first specimen well in fluid communication with the inlet and outlet ports and a second position to dispose the second specimen well in fluid communication with the inlet and outlet ports. The specimen tray is comprised of a pair of tray components each defining a respective one of the first and second wells and being jointly slideable between the first and second positions. The pair of tray components are separable from one another and each individually removable from the housing to allow one of the tray components to be removed during the medical procedure while the other of the tray components remains located in the housing for continuing to gather tissue specimens.

The separable and individually removeable tray components allow one of the specimen wells to be cleaned of gathered tissue specimens while the other specimen well remains in the housing for continued gathering of tissue specimens during the medical procedure. Accordingly, the pair of tray components can be shuttled into and out of the housing during a single medical procedure without losing a vacuum in the housing, thereby ensuring tissue specimens are not lost and improving the ability to gather multiple specimens in a single medical procedure in a more timely fashion.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 8 is a side perspective view of an inlet or outlet cover of the specimen collector for attachment to one of the inlet and outlet sleeves; and FIG. 9 is a front perspective view of the one of the tray components illustrating a coupling mechanism extending from a coupling end thereof.

DETAILED DESCRIPTION OF THE ENABLING EMBODIMENT

Referring to the figures, wherein like numerals indicate corresponding parts throughout the several views, a specimen collector 10 is generally shown for gathering specimens excised with a medical instrument 11 (schematically shown) such as an endoscope.

Figure 1:
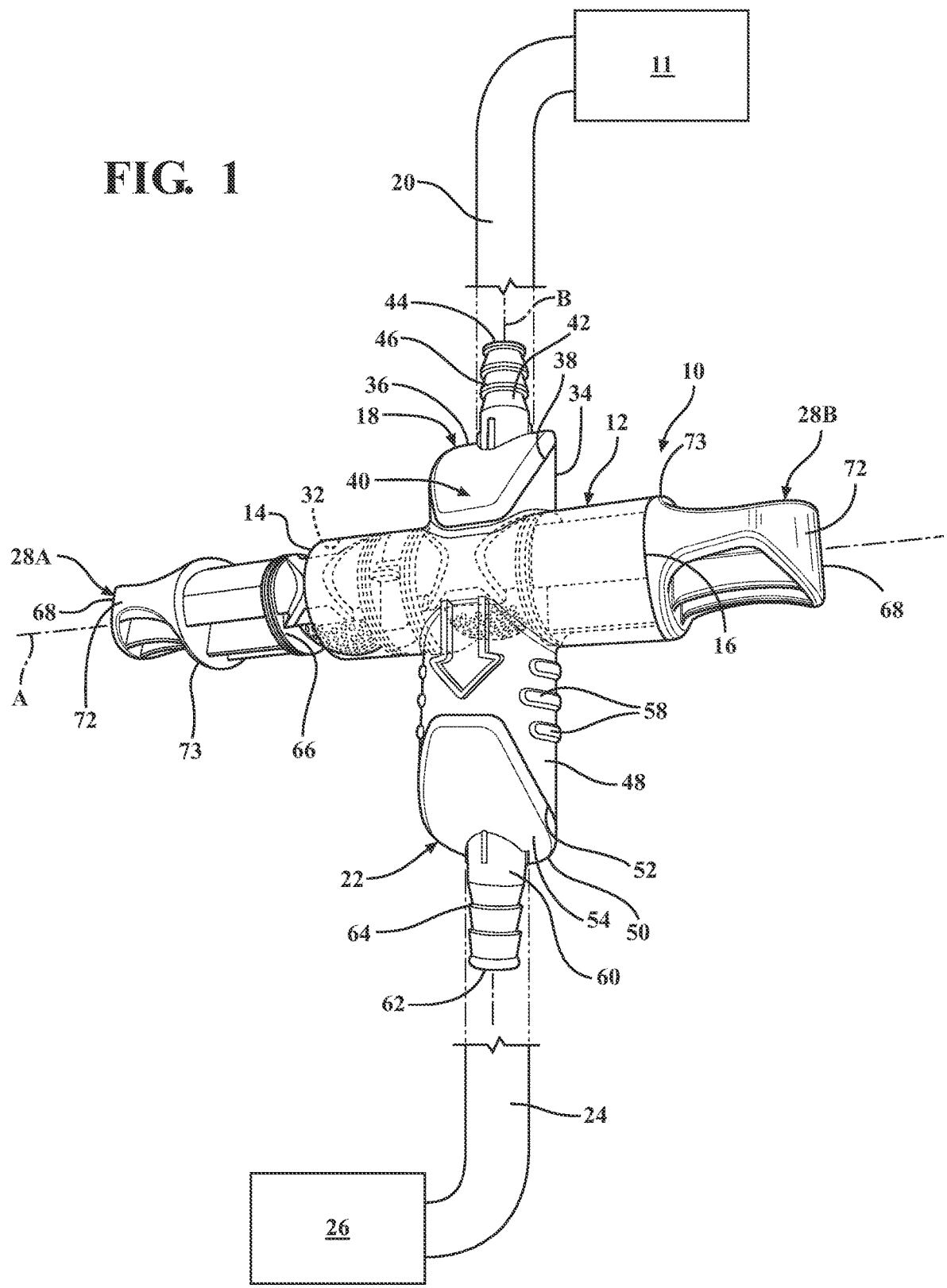
FIG. 1 is a front perspective view of a specimen collector illustrating a pair of tray components interlocked with one another and slideably disposed within a housing in a first position.
Figure 5:
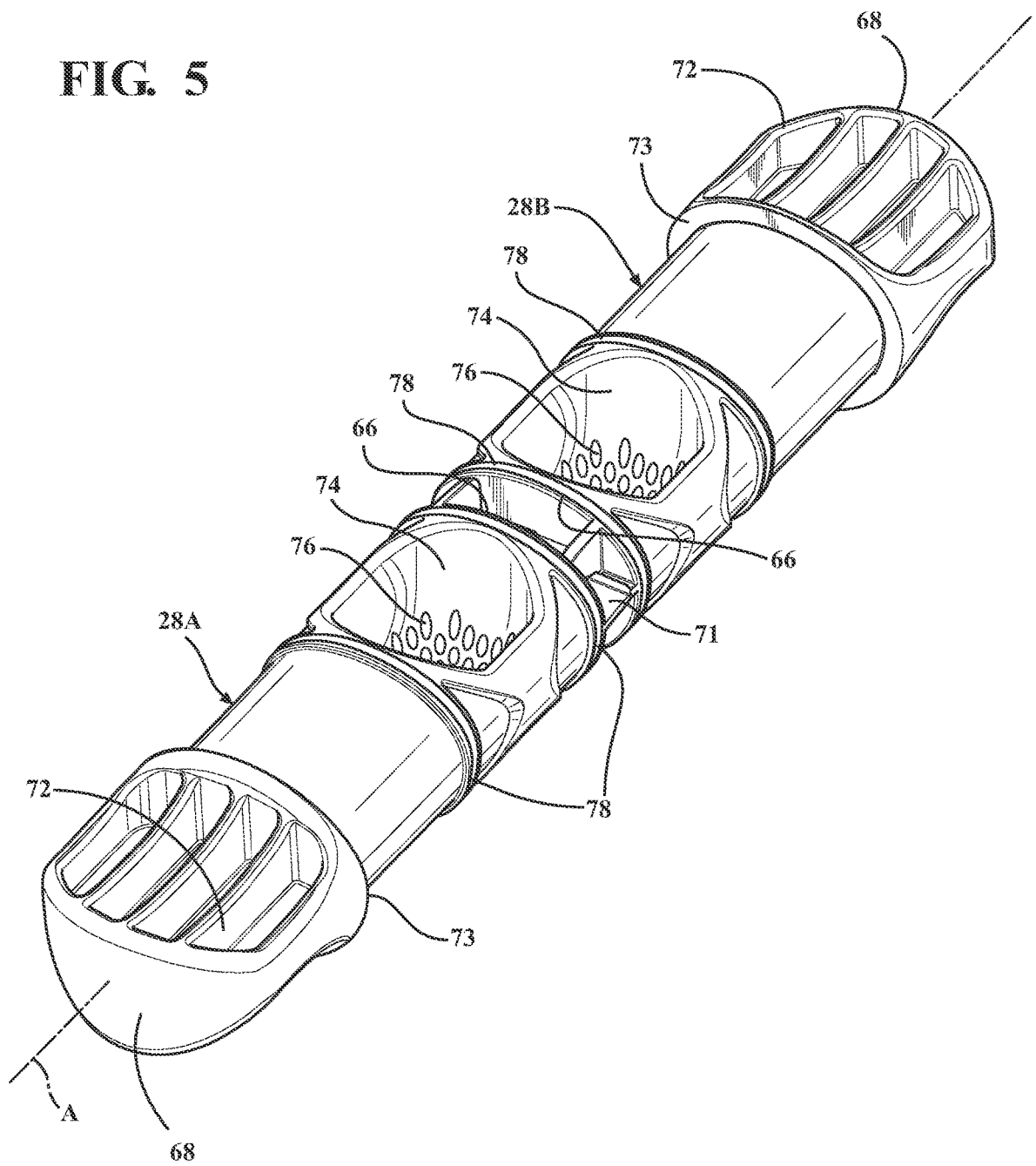
FIG. 5 is a front perspective view of the pair of tray components removed from the housing and disposed in an interlocked position.

As shown in FIG. 1, the specimen collector 10 includes a housing 12 that is generally conduit-shaped and extends along a first axis A between a first opening 14 and a second opening 16 to define a hollow interior 32. As will be discussed in greater detail below, the housing 12 has a non-circular cross-sectional shape taken along a plane being perpendicular to the first axis A. Specifically, in a preferred arrangement as best shown in FIG. 5, the housing 12 of the example embodiment has approximately an egg shape, but other shapes could be used. The housing 12 is made of a transparent material in order to allow collected specimens to be viewed during operation of the specimen collector 10.

Figure 6:
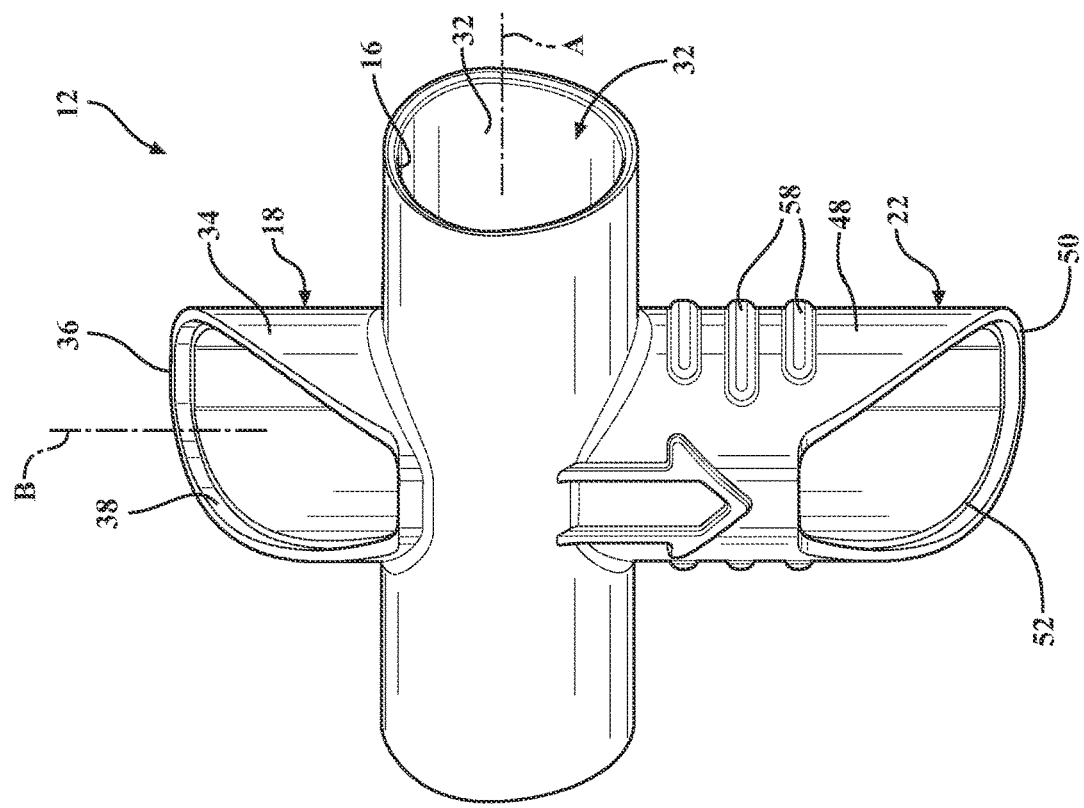
FIG. 6 is a front perspective view of the housing, illustrating first and second diameters of inlet and outlet of the housing.
Figure 7:
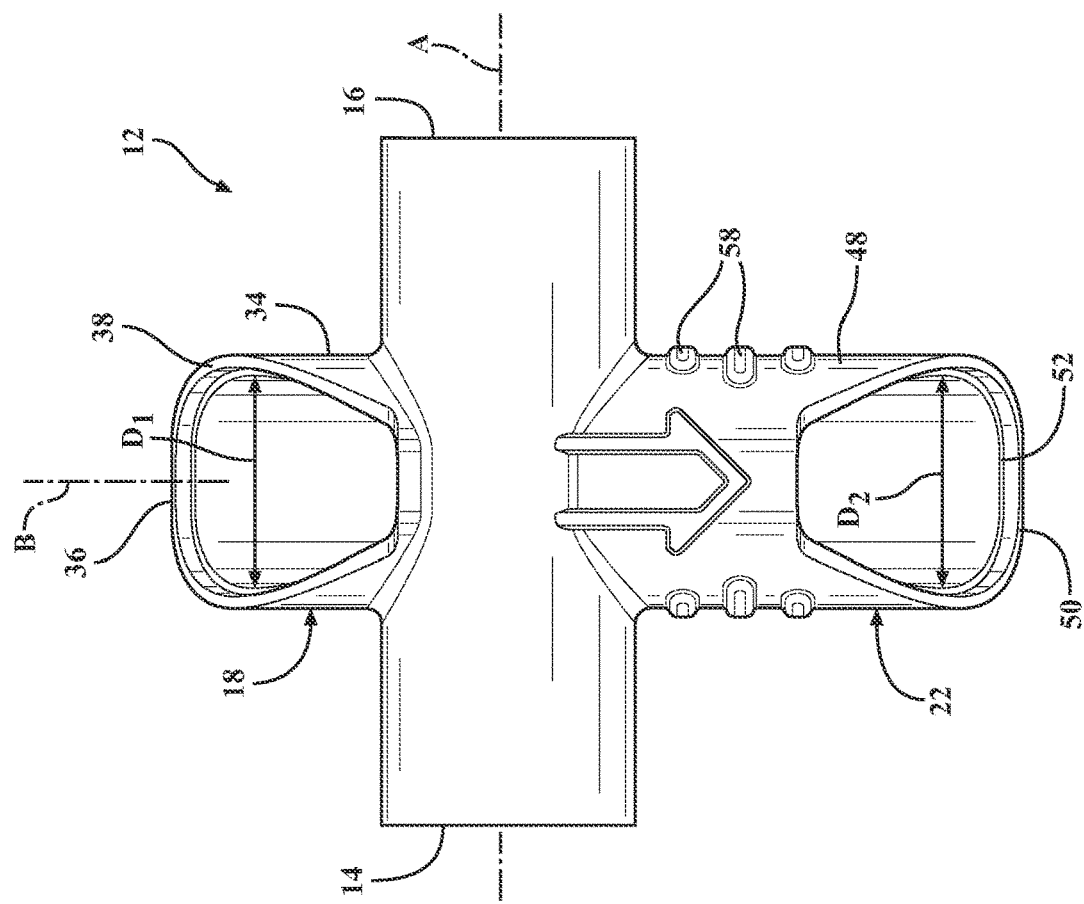
FIG. 7 is a side perspective view of the housing of FIG. 6, illustrating a non-circular cross-sectional shape of the housing.

An inlet port 18 extends from the housing 12 for coupling with a first conduit 20 to establish fluid communication between the medical instrument 11 and the hollow interior 32 of the housing 12 in order to pass air, fluid and tissue specimens collected by the medical instrument 11 to the hollow interior 32 of the housing. More particularly, the inlet port 18 includes an inlet sleeve 34 that extends from the housing 12 along a second axis B that is generally perpendicular to the first axis A and terminates at a first terminal end 36. As best shown in FIG. 6, the inlet sleeve 34 has an inlet diameter D1. An inlet mouth 38 is defined along the terminal end 36, and slopes downwardly from the terminal end 36 to the housing 12. As best shown in FIGS. 1-4 and 8, the inlet port 18 further includes an inlet cover 40 that overlies and closes the inlet mouth 38. The inlet cover 40 has a shape that corresponds with the inlet mouth 38 such that it seals the inlet mouth 38 when connected thereto. The inlet port 18 further includes an inlet fitting 42 that extends along the second axis B from the inlet cover 40 to an inlet opening 44. The inlet fitting 42 defines a plurality of inlet ribs 46 for allowing the first conduit 20 to be sealingly coupled with the inlet fitting 44.

The specimen collector 10 also includes an outlet port 22 that extends from the housing 12 for coupling with a second conduit 24 to establish fluid communication between the hollow interior 32 of the housing 12 and a suction source 26 (schematically shown) in order to create a suction effect at the medical instrument 11 and a vacuum within the hollow interior 32 of the housing 12. More particularly, the outlet port 22 includes an outlet sleeve 48 that extends from the housing 12 along the second axis B and terminates at a second terminal end 50. An outlet mouth 52 is defined along the second terminal end 50, and slopes downwardly from the second terminal end 50 toward the housing 12. As best shown in FIG. 6, the outlet sleeve 48 has an outlet diameter D2. The outlet port 22 further includes an outlet cover 54 having a shape that corresponds with the outlet mouth 52 such that the outlet cover 54 seals the outlet mouth 52 when connected thereto. The outlet sleeve 48 presents a plurality of sleeve ribs 58 for assisting an operator in gripping the specimen collector 10. The outlet port 22 further includes an outlet fitting 60 that extends along the second axis B from the outlet cover 54 to an outlet opening 62 and defines a plurality of outlet ribs 64 for allowing the second conduit 24 to be coupled with the outlet fitting 60.

The specimen collector 10 further includes a specimen tray 28A, 28B located in the hollow interior 32 that includes a first specimen well 74A and a second specimen well 74B, each for gathering tissue specimens that are collected by the medical instrument 11. As best shown in FIG. 9, each specimen well 74A, 74B preferably has a concave shape and defines an array of orifices 76, which allow specimens to be gathered while allowing air and fluid to pass through the specimen well 74A, 74B. In this manner, the specimen well 74A, 74B functions as a filter to trap the specimens. Each specimen well 74A, 74B has a well diameter D3 that is substantially equal to the inlet and outlet diameters D1, D2 to ensure that the specimen wells 74A, 74B are large enough to gather all specimens passed into the housing 12.

Figure 2:
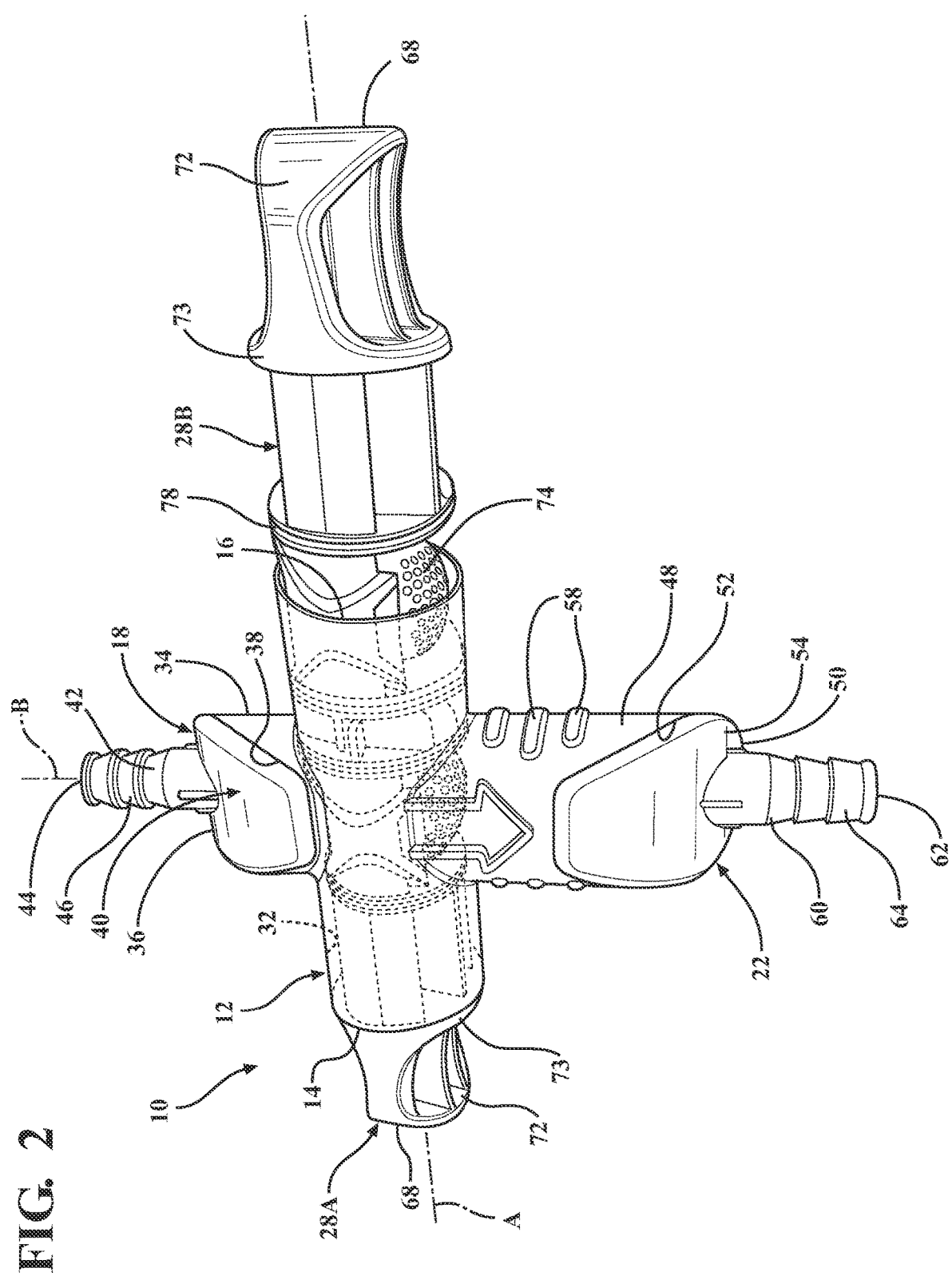
FIG. 2 is a front perspective view of the specimen collector illustrating the pair of tray components disposed in a second position within the housing.
Figure 4:
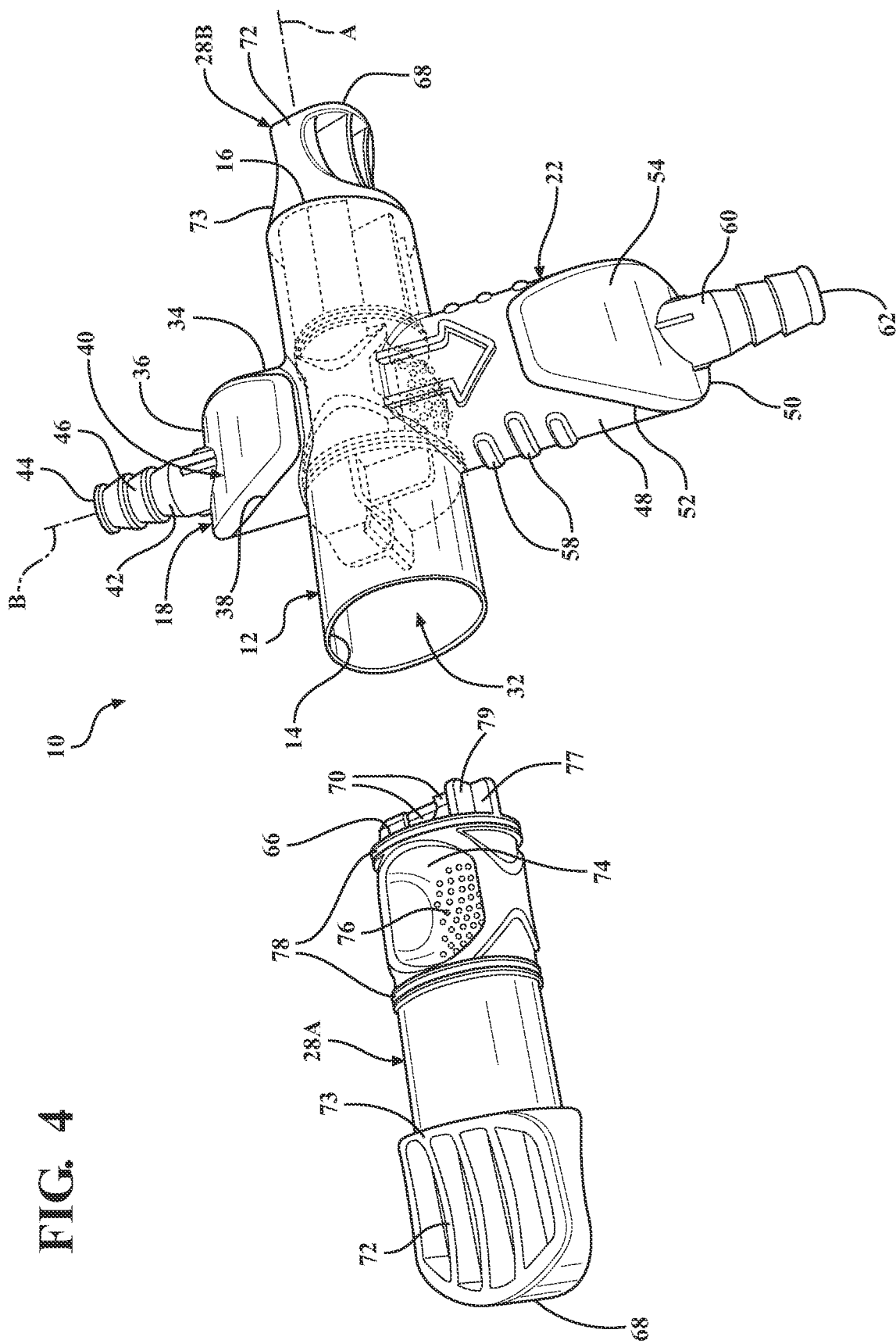
FIG. 4 is a front perspective view of the specimen collector illustrating the second tray component in the second position, and the first tray component after disconnection from the second tray component and removal from the housing.
Figure 3:
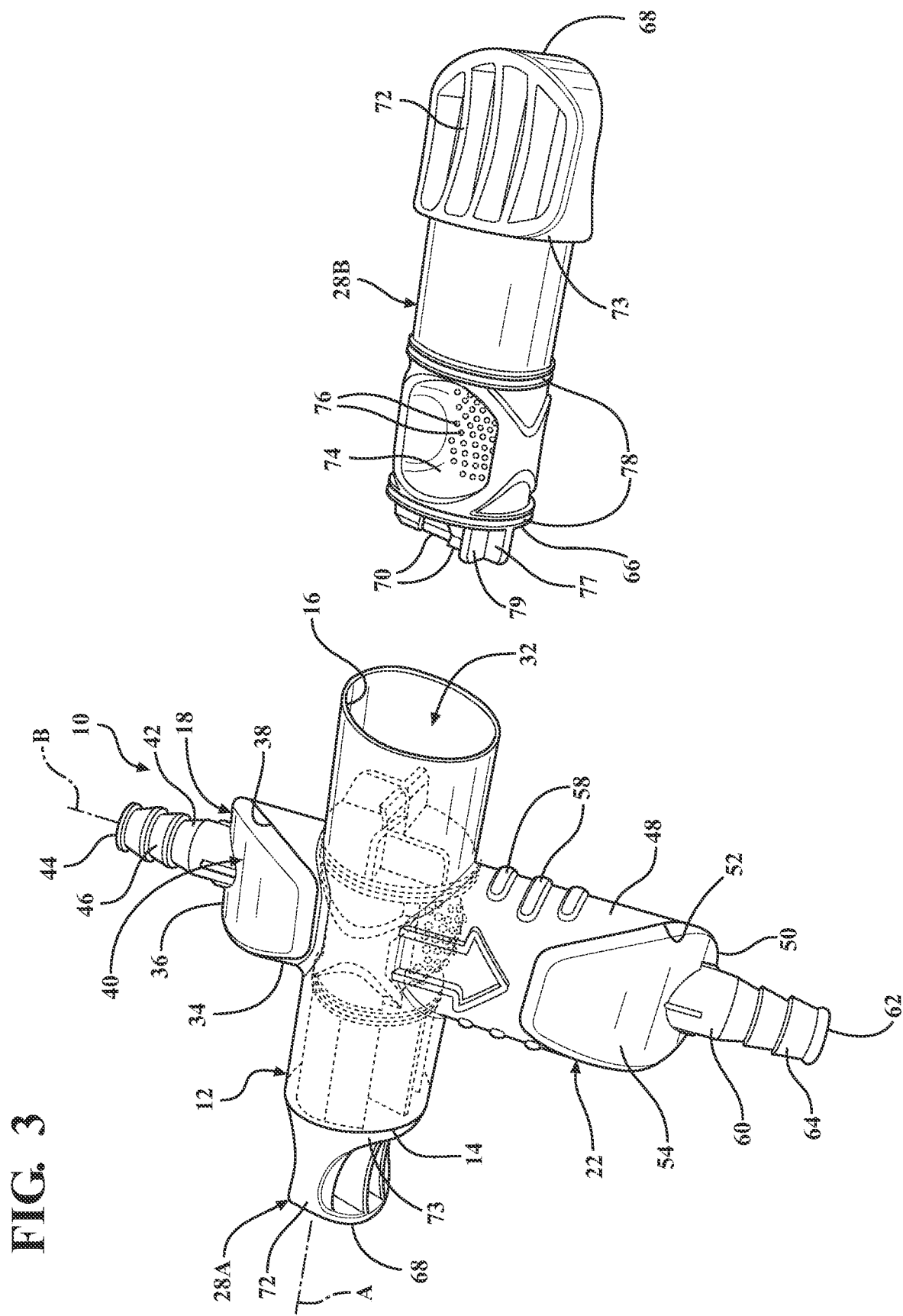
FIG. 3 is a front perspective view of the specimen collector illustrating a first tray component of the pair of tray components in the first position, and a second tray component of the pair of tray components after disconnection from the first tray component and removal from the housing.

The specimen tray 28A, 28B is comprised of a pair of tray components 28A, 28B that each include one of the first and second specimen wells 74A, 74B. The tray components 28A, 28B are jointly slideable along the first axis A between a first position and a second position. As shown in FIG. 1, in the first position, the first specimen well 74A is aligned relative to the first axis A with the inlet and outlet ports 18, 22 for gathering tissue specimens, and the second specimen well 74B is displaced relative to the first axis A from the inlet and outlet ports 18, 22. As shown in FIG. 2, in the second position, the second specimen well 74B is aligned relative to the first axis A with the inlet and outlet ports 18, 22 for gathering tissue specimens, and the first specimen well 74A is displaced relative to the first axis A from the inlet and outlet ports 18, 22.

The pair of tray components 28A, 28B are separable from one another and each individually removable from the housing 12 to allow one of the tray components 28A, 28B to be removed while the other of the tray components 28A, 28B remains located in the housing 12 in the first or second position. Accordingly, the tray components 28A, 28B may be shuttled into and out of the housing 12 into the first and second positions in this manner to provide continued gathering of the tissue specimens during a single medical procedure.

The pair of tray components 28A, 28B are selectively interlocked with one another in order to allow the tray components 28A, 28B to be jointly moved in forward (pushing) and backward (pulling) directions with one another in order to provide quick shuttling of the tray components 28A, 28B between the first and second positions, and placement into and out of the housing 12. More particularly, each of the tray components 28A, 28B extends along the first axis A between a coupling end 66 and a gripping end 68. While located in the housing 12, the tray components 28A, 28B are positioned in abutting end-to-end relationship with another at their coupling ends 66. As best illustrated in FIG. 9, a coupling mechanism 70, 77 extends from the coupling end 66 of each tray component 28A, 28B to establish a detachable interlocking connection between the tray components 28A, 28B. Each of the coupling mechanisms 70, 77 includes a plurality of central tabs 70 that are positioned side-by-side and diametrically aligned with one another along the first axis A. The central tabs 70 each extend axially from the coupling end 66 and have diametrically opposite wave shapes relative to one another. As best shown in FIGS. 1-2 and 5, the respective central tabs 70 of the pair of tray components 28A, 28B are radially and axially aligned with one another when the pair of tray components 28, 28B are received in the housing 12 in end-to-end relationship (e.g., FIG. 5) such that the central tabs 70 may be flexibly snapped into and out of connection with one another in response to the application of a predetermined axial force.

Each of the coupling mechanisms 70, 77 further includes a pair of outside tabs 77 that are diametrically aligned with one another outside of the central tabs 70. The outside tabs 77 each generally have an L-shape with horizontal and vertical members that extend perpendicularly to one another, and with the horizontal member extending generally parallel to the central tabs 70. When the pair of tray components 28A, 28B are received in the housing 12, the horizontal members of the respective outside tabs 77 circumferentially engage one another such that rotational movement of the pair of tray components 28A, 28B relative to one another is inhibited. Meanwhile, the vertical members of the outside tabs 77 structurally reinforce the horizontal members in the event that rotational forces are applied to the tray components 28A, 28B.

Each of the tray components 28A, 28B further includes a handle 72 that is located at the gripping end 68 and is located outside of the housing 12 with ergonomic finger grips for allowing a user to slide the tray components 28A, 28B within the housing 12 along the first axis A. The handles 72 are provided with ergonomic finger grips. The handles 12 each present a shoulder 73 that is radially aligned with the housing 12 at one of the first and second openings 14, 16 such that the shoulder 73 engages the housing 12 at one of the first and second openings 14, 16 upon the movement of the tray component 28A, 28B into the housing 12 to a respective one of the first and second positions. Put another way, the shoulders 73 limit the sliding movement of the tray components 28A, 28B within the housing 12, and are axially positioned such that they stop movement of the tray components 28A, 28B in the first and second positions to establish axially aligned relationship of the respective specimen wells 74 with the inlet and outlet ports 18, 22. Furthermore, the location of the shoulders 73 provides that when one of the specimen tray components 28A, 28B is pulled from the housing 12, the shoulder 73 of the other tray component 28A, 28B creates an opposing force which allows the tray components 28A, 28B to disconnect from one another at the central tabs 70 and leaves the other tray component 28A, 28B in the housing 12 in the first or second position.

As shown in FIG. 9, each of the tray components 28A, 28B further includes at least one sealing element 78 that seals the specimen well 74A, 74B within the housing 12 to prevent the vacuum within the housing 12 from being lost during shuttling of one of the first and second tray components 28A, 28B out of the housing 12. According to the example embodiment, the at least one sealing sealing element 78 includes a pair of O-ring seals 78 disposed on opposing sides of the specimen well 74A, 74B. As best shown in FIG. 9, a gap G1 is defined between the pair of O-ring seals 78 which is wider than the inlet diameter D1 and the outlet diameter D2 such that a large tissue specimen collection area is provided while also maintaining a seal about the entire specimen well 74A, 74B during operation.

As best shown in FIGS. 1 and 2, the pair of tray components 28A, 28B each have a non-circular cross-section taken along a plane being perpendicular to the first axis A that matches that of the hollow interior 32 of the housing 12 such that the pair of tray components 28A, 28B are only able to be inserted into respective openings 14, 16 of the housing 12 in a rotational position in which the specimen wells 74A, 74B are rotationally aligned with the inlet and outlet ports 18, 22 along the second axis B. This prevents incorrect, rotationally out of line insertion of the tray components 28A, 28B into the housing 12. This further allows quick shuttling of tray components 28A, 28B into and out of the housing 12 as the tray components 28A, 28B are biased into alignment during insertion thereof.

As best shown in FIGS. 1-5 and 9, the pair of tray components 28A, 28B are mirror images of one another, thus allowing the tray components 28A, 28B to be replaced by a new tray component 28A, 28B upon removal, thus facilitating the efficient acquisition of a large quantity of tissue specimens in a single operation. Differences between the tray components 28A, 28B may be present without departing from the scope of the subject disclosure.

Obviously, many modifications and variations of the present invention are possible in light of the above teachings and may be practiced otherwise than as specifically described while within the scope of the appended claims. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims.

What is claimed is:

1. A specimen collector for gathering tissue specimens during a medical procedure, comprising:
    a housing extending along a first axis between a first opening and a second opening to define a hollow interior;
    the housing including an inlet port and an outlet port each fluidly communicating with said hollow interior and located axially between said first and second openings;
    a specimen tray defining a first specimen well and a second specimen well and slideably disposed within said housing and axially slideable between a first position to dispose said first specimen well in fluid communication with said inlet and outlet ports and a second position to dispose said second specimen well in fluid communication with said inlet and outlet ports; and
    said specimen tray comprising a pair of tray components each defining a respective one of said first and second wells and jointly slideable between said first and second positions, said pair of tray components separable from one another and each individually removable from said housing to allow one of said pair of tray components to be removed during the medical procedure while the other of said pair of tray components remains located in said housing for continuing to gather tissue specimens.

2. The specimen collector as set forth in claim 1, wherein said pair of tray components are positioned in abutting relationship with one another within said housing to facilitate shuttling movement between said first and second positions.

3. The specimen collector as set forth in claim 2, wherein said pair of tray components each extend from a gripping end to a coupling end, and a coupling mechanism extends from said coupling end to establish a detachable connection between said pair of tray components when said pair of tray components are disposed in said abutting relationship.

4. The specimen collector as set forth in claim 3, wherein said coupling mechanism of each tray component includes a pair of central tabs diametrically aligned, and each of said central tabs having a diametrically opposite wave shape such that when said pair of tray components are received in said housing said central tabs of said pair of tray components are axially aligned with one another and snapped into connection with one another to establish said detachable connection.

5. The specimen collector as set forth in claim 4, wherein said coupling mechanism of each of said tray components further include a pair of outside tabs each disposed radially outside of a respective one of said central tabs, and wherein said outside tabs of said respective pair of tray components circumferentially overly one another when said pair of tray components are received in said housing such that said outside tabs inhibit rotational movement of said pair of tray components relative to one another.

6. The specimen collector as set forth in claim 1, wherein said pair of tray components each have a shoulder located outside of said housing and radially aligned with said housing such that said shoulder engages said housing at one of said first and second openings upon movement of said tray component into said housing to one of a plurality of predetermined positions.

7. The specimen collector as set forth in claim 6, wherein said plurality of predetermined positions includes said first and second positions with one of said specimen wells aligned relative to said first axis with said inlet and said outlet.

8. The specimen collector as set forth in claim 7, wherein each of said tray components includes a handle disposed between a gripping end and said shoulder and having ergonomic grips for allowing an operator to slide said pair of tray components within and out of said housing.

9. The specimen collector as set forth in claim 1, wherein said housing and said pair of tray components have corresponding non-circular cross-sectional shapes along a plane being perpendicular to said first axis for preventing rotation of said pair of tray components relative to said housing while slideably disposed within said housing and ensuring rotationally aligned relationship of said pair of tray components.

10. The specimen collector as set forth in claim 9, wherein said corresponding cross-sectional shapes of the housing and tray components are each an egg shape.

11. The specimen collector as set forth in claim 1, wherein each of said tray components includes at least one sealing element to seal the respective one of said first and second specimen wells with said housing and to maintain a vacuum when the other of said tray components is individually removed from said housing.

12. The specimen collector as set forth in claim 11, wherein said at least one sealing element of each of said tray components includes a pair of O-ring seals extending about opposing sides of said respective first and second specimen wells of said tray components.

13. The specimen collector as set forth in claim 12, wherein a gap is defined between said pair of O-ring seals being wider than a width of said inlet and outlet ports.

14. The specimen collector as set forth in claim 1, wherein said housing is comprised of a transparent material for allowing the gathered tissue specimens to be viewable during the medical procedure.

15. The specimen collector as set forth in claim 1, wherein said pair of tray components are mirror images of one another.

16. The specimen collector as set forth in claim 1, wherein said inlet port includes an inlet sleeve extending from said housing, said outlet port includes an outlet sleeve extending from said housing, said inlet sleeve has an inlet diameter, said outlet sleeve has an outlet diameter, said first and second specimen wells each have a well diameter, and wherein said well diameter is substantially equal to said inlet and outlet diameters.

17. The specimen collector as set forth in claim 1 wherein said first and second specimen wells each have a concave shape and define an array of orifices allowing tissue specimens to be gathered while allowing air and fluid to pass through said specimen wells.

18. The specimen collector as set forth in claim 1, wherein said inlet and outlet ports are each disposed along a second axis being generally perpendicular to said first axis.

19. The specimen collector as set forth in claim 18, wherein when said specimen tray components are located in said first position, said first specimen well is aligned with said inlet and outlet ports along said second axis, and when said specimen tray components are located in said second position, said second specimen well is aligned with said inlet and outlet ports along said second axis.

\* \* \* \* \*